United States Patent
Niccum

(10) Patent No.: US 9,745,519 B2
(45) Date of Patent: Aug. 29, 2017

(54) FCC PROCESS USING A MODIFIED CATALYST

(71) Applicant: Phillip K Niccum, Houston, TX (US)

(72) Inventor: Phillip K Niccum, Houston, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 772 days.

(21) Appl. No.: 13/973,648

(22) Filed: Aug. 22, 2013

(65) Prior Publication Data

US 2015/0057482 A1   Feb. 26, 2015

Related U.S. Application Data

(60) Provisional application No. 61/691,865, filed on Aug. 22, 2012.

(51) Int. Cl.
    *C07C 4/06*     (2006.01)
    *C10G 11/18*    (2006.01)
    (Continued)

(52) U.S. Cl.
    CPC .......... *C10G 11/182* (2013.01); *B01J 29/084* (2013.01); *B01J 29/40* (2013.01); *B01J 29/80* (2013.01);
    (Continued)

(58) Field of Classification Search
    CPC .. C10G 9/00; C10G 11/182; C10G 2300/708; C07C 4/06; B01J 29/084; B01J 29/40;
    (Continued)

(56) References Cited

U.S. PATENT DOCUMENTS

| | | |
|---|---|---|
| 4,717,466 A | 1/1988 | Herbst et al. |
| 4,778,661 A | 10/1988 | Avidan et al. |

(Continued)

FOREIGN PATENT DOCUMENTS

| | | |
|---|---|---|
| EP | 0395345 | 10/1990 |
| EP | 0519625 | 12/1992 |

(Continued)

OTHER PUBLICATIONS

Phillip K. Niccum, Rik B. Miller, Alan M. Claude, Michael A. Silverman, Nazeer A. Bhore, Ke Liu, Girish K. Chitnis, Steven J. McCarthey, Maxofin: A Novel FCC Process for Maximizing Light Olefins using a New Generation of ZSM-5 Additive, NPRA Paper AM-98-18, San Francisco, California, Mar. 15-17, 1998.

(Continued)

*Primary Examiner* — Sharon Pregler
(74) *Attorney, Agent, or Firm* — Gary Machetta

(57) ABSTRACT

Methods and systems for producing a hydrocarbon are provided. The method can include cracking one or more $C_2$-$C_{10}$ hydrocarbons in the presence of a catalyst under conditions sufficient to produce an effluent containing ethylene, propylene, gasoline, and a coked-catalyst, wherein the catalyst includes a first catalytic component having an average pore size of less than 6.4 Å and a second catalytic component having an average pore size of 6.4 Å or more, separating the effluent to provide a recovered coked-catalyst and a cracked product; and regenerating the recovered coked-catalyst to produce heat and the catalyst.

18 Claims, 1 Drawing Sheet

(51) Int. Cl.
*B01J 38/02* (2006.01)
*B01J 38/12* (2006.01)
*B01J 29/08* (2006.01)
*B01J 29/40* (2006.01)
*B01J 29/80* (2006.01)
*B01J 29/90* (2006.01)

(52) U.S. Cl.
CPC ............... *B01J 29/90* (2013.01); *B01J 38/02* (2013.01); *B01J 38/12* (2013.01); *C10G 2300/708* (2013.01)

(58) Field of Classification Search
CPC ... B01J 29/80; B01J 29/90; B01J 38/02; B01J 38/12
USPC ......... 208/106, 113, 114, 119, 120; 585/653, 585/651, 648, 644, 650
See application file for complete search history.

(56) References Cited

U.S. PATENT DOCUMENTS

| | | | |
|---|---|---|---|
| 4,830,728 A | 5/1989 | Herbst et al. | |
| 4,831,205 A | 5/1989 | Krambeck et al. | |
| 4,855,521 A | 8/1989 | Avidan et al. | |
| 4,933,069 A | 6/1990 | Huss et al. | |
| 4,980,053 A | 12/1990 | Li et al. | |
| 5,006,497 A | 4/1991 | Herbst et al. | |
| 5,043,522 A | 8/1991 | Leyshon et al. | |
| 5,055,176 A | 10/1991 | Herbst et al. | |
| 5,055,473 A | 10/1991 | Arrowsmith et al. | |
| 5,171,921 A | 12/1992 | Gaffney et al. | |
| 5,179,054 A | 1/1993 | Schipper et al. | |
| 5,232,580 A | 8/1993 | Le et al. | |
| 5,258,114 A | 11/1993 | Aufdembrink et al. | |
| 5,286,370 A | 2/1994 | Chu et al. | |
| 5,389,232 A | 2/1995 | Adewuyi et al. | |
| 5,395,512 A | 3/1995 | Hsing et al. | |
| 5,968,342 A | 10/1999 | Tsunoda et al. | |
| 5,997,728 A | 12/1999 | Adewuyi et al. | |
| 6,069,287 A | 5/2000 | Ladwig et al. | |
| 6,083,867 A | 7/2000 | Wu et al. | |
| 6,093,867 A | 7/2000 | Ladwig et al. | |
| 6,106,697 A | 8/2000 | Swan et al. | |
| 6,113,776 A | 9/2000 | Upson | |
| 6,153,089 A | 11/2000 | Das et al. | |
| 6,218,590 B1 | 4/2001 | Yao et al. | |
| 6,222,087 B1 | 4/2001 | Johnson et al. | |
| 6,313,366 B1 | 11/2001 | Ladwig et al. | |
| 6,339,180 B1 | 1/2002 | Ladwig et al. | |
| 6,388,152 B1 | 5/2002 | Ladwig et al. | |
| 6,455,750 B1 | 9/2002 | Steffens et al. | |
| 6,514,896 B1 | 2/2003 | Drake et al. | |
| 6,538,169 B1 | 3/2003 | Pittman et al. | |
| 6,646,176 B1 | 11/2003 | Dath et al. | |
| 6,649,802 B1 | 11/2003 | Frame et al. | |
| 6,656,345 B1 | 12/2003 | Chen et al. | |
| 6,709,572 B2 | 3/2004 | Corma | |
| 6,867,341 B1 | 3/2005 | Abrevaya et al. | |
| 6,916,757 B2 | 7/2005 | Ziebarth et al. | |
| 6,951,968 B1 | 10/2005 | Dath et al. | |
| 6,977,321 B1 | 12/2005 | Dath et al. | |
| 7,011,740 B2 | 3/2006 | Tallman et al. | |
| 7,128,827 B2 | 10/2006 | Tallman et al. | |
| 7,153,479 B2 | 12/2006 | Peterson et al. | |
| 7,229,548 B2 * | 6/2007 | Riley .................. | B01J 23/85 208/113 |
| 7,261,807 B2 | 8/2007 | Henry et al. | |
| 7,267,759 B2 | 9/2007 | Chen et al. | |
| 7,270,739 B2 | 9/2007 | Chen et al. | |
| 7,271,304 B2 | 9/2007 | Du Toit | |
| 7,301,065 B2 | 11/2007 | Vaughn et al. | |
| 7,312,370 B2 | 12/2007 | Pittman et al. | |
| 7,314,964 B2 | 1/2008 | Abrevaya et al. | |
| 7,326,332 B2 | 2/2008 | Chen et al. | |
| 7,425,258 B2 | 9/2008 | Chen et al. | |
| 7,425,663 B2 | 9/2008 | Bach et al. | |
| 7,435,331 B2 | 10/2008 | Peterson et al. | |
| 7,446,071 B2 | 11/2008 | Abrevaya et al. | |
| 7,459,596 B1 | 12/2008 | Abrevaya et al. | |
| 7,488,700 B2 | 2/2009 | Choi et al. | |
| 7,491,315 B2 | 2/2009 | Eng et al. | |
| 7,585,489 B2 | 9/2009 | Abrevaya et al. | |
| 7,589,244 B2 | 9/2009 | Coupard et al. | |
| 7,611,622 B2 | 11/2009 | Niccum et al. | |
| 7,615,143 B2 | 11/2009 | Chen et al. | |
| 7,718,840 B2 | 5/2010 | Choi et al. | |
| 7,728,185 B2 | 6/2010 | Senetar et al. | |
| 7,754,934 B2 | 7/2010 | Tsunoda et al. | |
| 7,820,033 B2 | 10/2010 | Eng et al. | |
| 7,884,257 B2 | 2/2011 | Takamatsu et al. | |
| 7,893,311 B2 | 2/2011 | Takamatsu et al. | |
| 7,906,077 B2 | 3/2011 | Sandacz | |
| 7,923,591 B2 | 4/2011 | Birke et al. | |
| 7,939,702 B2 | 5/2011 | Choi et al. | |
| 7,943,038 B2 | 5/2011 | Ramamurthy | |
| 2002/0003103 A1 | 1/2002 | Henry et al. | |
| 2002/0189973 A1 | 12/2002 | Henry et al. | |
| 2005/0150817 A1 | 7/2005 | Tallman et al. | |
| 2006/0042999 A1 | 3/2006 | Iqbal et al. | |
| 2006/0049082 A1 | 3/2006 | Niccum et al. | |
| 2007/0010699 A1 | 1/2007 | Choi et al. | |
| 2007/0082809 A1 | 4/2007 | Choi et al. | |
| 2008/0073907 A1 | 3/2008 | Niccum | |
| 2008/0223754 A1 | 9/2008 | Subramanian et al. | |
| 2008/0230442 A1 | 9/2008 | Iqbal et al. | |
| 2008/0318764 A1 | 12/2008 | Abrevaya et al. | |
| 2009/0299118 A1 | 12/2009 | Claude | |
| 2009/0299119 A1 | 12/2009 | Claude | |
| 2010/0105974 A1 | 4/2010 | Towler et al. | |
| 2011/0152594 A1 | 6/2011 | Brown | |
| 2011/0251046 A1 | 10/2011 | Niccum et al. | |
| 2011/0251047 A1 | 10/2011 | Niccum et al. | |
| 2011/0253600 A1 | 10/2011 | Niccum | |
| 2011/0257005 A1 | 10/2011 | Niccum | |
| 2011/0303582 A1 | 12/2011 | Niccum et al. | |
| 2012/0165591 A1 | 6/2012 | Tallman | |
| 2013/0079569 A1 * | 3/2013 | Mehlberg .............. | C10G 51/026 585/302 |
| 2013/0317271 A1 * | 11/2013 | Al-Ghrami ............ | B01J 38/00 585/653 |

FOREIGN PATENT DOCUMENTS

| | | |
|---|---|---|
| EP | 1525174 | 4/2005 |
| EP | 2053021 | 4/2009 |
| WO | 03051510 | 6/2003 |
| WO | 2007043741 | 4/2007 |
| WO | 2007043742 | 4/2007 |
| WO | 2009039948 | 4/2009 |
| WO | 2010021910 | 2/2010 |

OTHER PUBLICATIONS

Michael J. Tallman, Curtis N. Eng, Propylene on Purpose, Dec. 2010, Hydrocarbon Engineering.
Bottoms Cracking Additive, Intercat, Sea Girt, New Jersey.
Lance D. Silverman, Steven Winkler, Jack A. Tiethof, Anatol Witoshkin, Matrix Effects in Catalytic Cracking, 1986 NPRA Annual Meeting, Mar. 23-25, 1986.
Amos A. Avidan, Michael Edwards, Hartley Owen, Innovative Improvements Highlight FCC's Past and Future, , 1990 Oil & Gas Journal.
Raul F. Lobo, Introduction to the Structural Chemistry of Zeolites, 2003 Marcel Dekker, Inc.

* cited by examiner

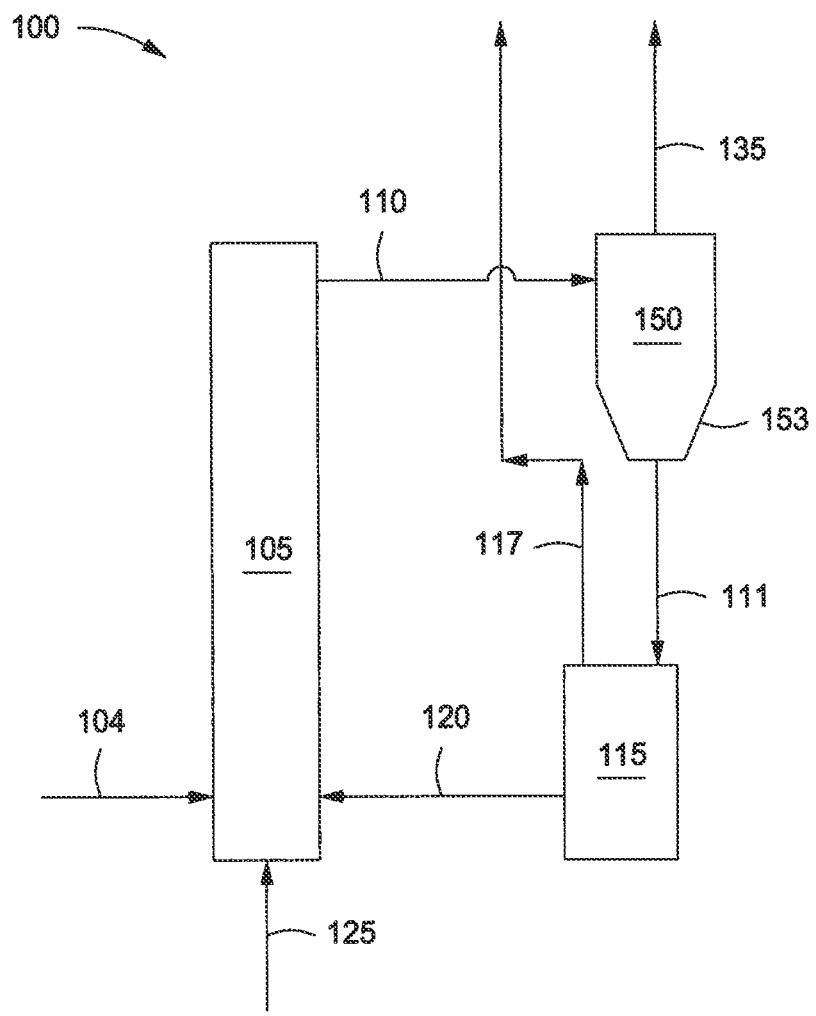

FCC PROCESS USING A MODIFIED CATALYST

CROSS-REFERENCE TO RELATED APPLICATION

This application claims priority to U.S. Provisional Patent Application having Ser. No. 61/697,865, filed on Aug. 22, 2012, which is incorporated by reference herein.

BACKGROUND

Field

Embodiments described herein generally relate to methods and systems for fluidized catalytic cracking. More particularly, such embodiments relate to methods and systems for fluidized catalytic cracking using modified catalysts.

Description of the Related Art

Fluid Catalytic Cracking (FCC) is a technology used in refineries to produce transportation fuels such as gasoline and distillates and other liquid and/or gaseous hydrocarbon products from higher molecular weight feedstocks. The FCC process uses a reactor called a riser, essentially a pipe, in which a hydrocarbon is contacted with fluidized catalyst particles to effect the conversion of the hydrocarbon to more valuable products. For example, the FCC unit can convert gas oil by "cracking" the gas oil molecules into smaller molecules. The resulting hydrocarbon product and catalyst mixture both flow through the reactor, hence the term fluid catalytic cracking.

For the catalytic cracking of traditional refinery gas oil feedstocks such as atmospheric and vacuum gas oils, catalysts, such as catalysts containing Y or USY zeolites, are used with pore diameters large enough to allow diffusion of the feed and products into and out of the catalyst.

For heavy FCC feedstocks, such as atmospheric residue or vacuum residue containing feedstocks, the pore diameters of these zeolites may be too small to allow diffusion of the largest feed molecules into the active sites within the zeolites. Therefore, for heavy FCC feedstocks, catalytically active non-zeolitic materials, such as various forms of amorphous alumina and powdered clays with even larger pore sizes, are often included in the catalysts to allow the largest molecules to crack to some extent on non-zeolite surfaces so that the fragments can then diffuse into the smaller zeolite pores for further cracking. These catalysts are commonly referred to as catalysts with active matrices. The product selectivity from cracking on the non-zeolite catalytic materials are generally not as favorable for the production of the most desired FCC products and produce higher yields of coke and light gases compared to the zeolite catalyzed cracking. Therefore, the catalysts employed in processing of very heavy FCC feedstocks are often formulated with the intent to provide a balance between the zeolite and active matrix contributions to the catalytic surface areas.

For the catalytic cracking of light feeds such as liquefied petroleum gas (LPG) or light naphtha, in the absence of heavier feed components, smaller pore diameter zeolites, such as ZSM-5, sometimes referred to as medium pore zeolites, are typically employed. These zeolites have greater activity for cracking the light feeds than do the larger pore size zeolites, and limitations to diffusion of feedstock molecules or product molecules larger than those present in the feedstock into the zeolite has not been considered a relevant issue.

The feedstock entering the riser is heated to the desired cracking temperature because the cracking reactions are endothermic. During the cracking of heavy feeds coke is formed within the catalyst. The coke deposits are typically burned with an oxygen source such as air in a regenerator. Burning the coke is an exothermic process that can supply the heat needed for the cracking process. In a heat balanced operation, typical of most FCC operations, the quantity of coke formed on the catalyst is significant enough that no external heat source or fuel is needed to supplement the heat from coke combustion.

On the other hand, unlike heavy feeds, light feeds do not deposit enough coke on the catalyst in the reactor to support the proper heat balance of the FCC unit. In these cases, an external source of fuel or other heat input can be required to keep the FCC unit in heat balance. Adding external heating sources or fuel directly to the regenerator of the FCC unit can increase the capital cost, operational expenditures, and/or complexity of the process. At the same time, because of the extremely high reaction temperatures employed in cracking light feedstocks, coke can be aggressively deposited or formed in the FCC reactor hardware. This coke can damage refractory in the FCC hardware and/or plug the internals of the reactor. The extent of this coking can be severe enough to require shutdown to remove the accumulated coke and replace or repair the damaged refractory.

The high temperatures employed in catalytic cracking of light feedstocks can also produce a gasoline product with unacceptably high concentrations of dienes, other olefins, and/or other reactive species that can cause the gasoline product to fail compliance with applicable motor fuel quality specifications such as potential gum formation as determined by ASTM D-525 and ASTM D-873.

There is a need, therefore, for more improved methods and systems for cracking light hydrocarbon feeds with a reduced need for external heating, a reduced diene and/or other olefin concentration in the hydrocarbon products, and/or a reduced propensity to foment coke formation and/or coke deposits within the system.

BRIEF DESCRIPTION OF THE DRAWINGS

FIG. 1 depicts a schematic of an illustrative fluid catalytic cracking system, according to one or more embodiments described.

DETAILED DESCRIPTION

Methods and systems for fluid catalytic cracking are provided. The method for fluid catalytic cracking can include cracking a $C_2$-$C_{10}$ hydrocarbon in the presence of a catalyst under conditions sufficient to produce an effluent that includes ethylene, propylene, naphtha, or any combination thereof and a coked-catalyst. The catalyst can include a first catalytic component having an average pore size of less than 6.4 Å and a second catalytic component having an average pore size of 6.4 Å or more. The method can also include separating the effluent to provide a recovered coked-catalyst and a cracked product and regenerating the recovered coked-catalyst to produce heat and the catalyst.

It has been surprisingly and unexpectedly discovered that adding a catalytically active larger pore size component to a smaller pore size catalyst in a reaction riser of an FCC unit for cracking light hydrocarbon feeds can increase the deposition of coke on the catalyst particles and reduce the diene and/or other olefin concentration(s) in the reactor product. The use of both the larger and smaller pore size catalytically active surfaces thus reduce or eliminate coke formation on the reaction equipment. The use of both smaller and larger pore sized catalytically active surfaces can also reduce or eliminate the need for supplemental fuel to the regenerator, in part, because of the heat produced by burning the increased coke deposited on the catalyst in the regenerator. The mixture of catalyst sizes can also improve the quality of the gasoline product by lowering its diene and/or other olefin content. Coke deposits in the reactor can also be reduced, thus reducing coke induced equipment damage and/or plugging.

The term "pore size" or "average pore size," as used herein, refers to the unit cell size as determined by ASTM D 3942. As used herein, the term "first catalytic component" and "smaller pore component" are used interchangeably and refer to a catalytically active material having an average pore size of less than 6.4 Å. As used herein, the term "second catalytic component" and "larger pore component" are used interchangeably and refer to a catalytically active material having an average pore size equal to or greater than 6.4 Å. As used herein, the term "catalytically active material" refers to a material having catalytically active sites for promoting reactions such as cracking, isomerization, oligomerization, cyclization, dehydrogenation, and/or polymerization of hydrocarbons.

The increased formation or deposition of coke on the catalyst particles has been found to correlate with a decrease in the amount of coke precursors in the riser effluent. The decreased presence of coke precursors in the riser effluent can reduce formation of coke in the downstream equipment including transfer lines and separators and the attendant plugging of the reactor. The decreased presence of coke in the downstream equipment can reduce or eliminate coke induced damage to the refractory in the downstream equipment and thus can reduce the likelihood of failure of the downstream equipment.

The dienes, other olefins, and/or other coke precursors, if present, in the light hydrocarbon feed and/or if formed in the reaction riser of the FCC unit can oligomerize to form successively larger multi-ring aromatic molecules or structures on and/or within the second catalytic component of the catalyst to form coke on and/or within the catalyst. The coke forming reactions resulting in the multi-ring aromatic structures from low molecular weight dienes, other olefins, and/or other coke precursors can include, but are not limited to, oligomerization, cyclization, and dehydrogenation reactions. The coke present on the catalyst can remain with the catalyst when the cracked product of the riser effluent is separated from the coked-catalyst. As such, the amount of the dienes, other olefins, and/or other coke precursors can be reduced or prevented from contaminating the recovered cracked product since the coke on the catalyst is a product of consumed coke precursors. The reduction in coke precursors, such as olefins and especially dienes, in the cracked product from the use of a catalyst having a first catalytic component and a second pore catalytic component as compared to a catalyst having only a first or smaller pore catalytic component, can also enable the gasoline product to more closely meet required fuel specifications.

Lower molecular weight dienes and olefins can be byproducts created by the cracking of the feedstock on the smaller pore size first catalytic component. Increasingly large coke precursors can be formed as a result of continuing oligomerization, cyclization, and/or dehydrogenation reactions with lower molecular weight dienes and olefins. Thus, the presence of the large pore catalytically active surfaces can provide an avenue for the capture of increasingly large coke precursors in the reaction mixture that become too large for diffusion into the smaller pore size catalytic surfaces of the first catalytic component. These increasingly large coke precursors continue undergoing oligomerization, cyclization, and/or dehydrogenation to ultimately form coke on the catalyst. The diene and/or other olefin byproducts can be converted to coke on the catalyst due to the presence of the second catalytic component.

FIG. 1 depicts a schematic of an illustrative fluid catalytic cracking ("FCC") system 100, according to one or more embodiments. The FCC system 100 can include one or more risers or reaction risers 105, one or more ducts or transfer lines 110, one or more separators 150, and one or more regenerators 115. Although not shown, the FCC system 100 can also include one or more strippers. A hydrocarbon or feed via line 104 and a catalyst via line 120 can be introduced to the reaction riser 105. The hydrocarbon can be cracked within the reaction riser 105 in the presence of the catalyst under conditions sufficient to form a cracked product and coked catalyst mixture or "riser effluent." The cracked product can be or include ethylene, propylene, naphtha, or any combination thereof. The riser effluent can be recovered via line 110 from the reaction riser 105.

The catalyst in line 120 can be or include any catalyst suitable for the conversion of hydrocarbons to olefins. The catalyst in line 120 can be one that favors the production of propylene and/or ethylene within the reaction riser 105 from the hydrocarbons introduced thereto. For the cracking of light hydrocarbons, one or more zeolite catalysts, e.g., crystalline zeolite molecular sieves, containing both silica and alumina, can be used for the fluidized catalytic cracking. The zeolite catalyst can also be used with one or more modifiers such as phosphorous. The zeolite catalyst can also be used in conjunction with other known catalysts useful in fluidized catalytic cracking. Illustrative catalysts can include, but are not limited to, ZSM-5, ZSM-11, ZSM-12, ZSM-22, ZSM-23, ZSM-35, ZSM-48, ZSM-57, X-type zeolites (zeolite X), Y-type zeolites (zeolite Y), USY, REY, RE-USY, MCM-9, MCM-22, MCM-41, silicoaluminophosphate (SAPO) molecular sieves, faujasite, mordenite, and other synthetic and naturally occurring zeolites and mixtures thereof.

The catalyst in line 120 can include the first or "smaller pore" catalytic component and the second or "larger pore" catalytic component. For example, the first catalytic component can have an average pore size from a low of about 2 Å, about 4 Å, about 4.8 Å, about 5.2 Å, or about 5.4 Å to a high of about 5.5 Å, about 5.6 Å, about 5.8 Å, about 6 Å, about 6.2 Å, or about 6.3 Å. In another example, the first catalytic component can have an average pore size from about 2 Å to about 6.2 Å, from about 5 Å to about 6 Å, from about 5.2 Å to about 5.8 Å, or from about 5.4 Å to about 5.6 Å. The second catalytic component can have an average pore size from a low of 6.4 Å, about 8 Å, about 10 Å, about 15 Å, about 20 Å, or about 23 Å to a high of about 25 Å, about 28 Å, about 30 Å, about 35 Å, about 40 Å, or about 50 Å. In another example, the second catalytic component can have an average pore size of about 6.4 Å to about 50 Å, from about 15 Å to about 40 Å, from about 20 Å to about 30 Å, or from about 24 Å to about 26 Å.

The first catalytic component can include a zeolite. For example, the first catalytic component can be, but is not limited to, ZSM-5, ZSM-11, ZSM-12, ZSM-22, ZSM-23, ZSM-35, ZSM-48, or any combination thereof. In an example, the first catalytic component can be ZSM-5. The second catalytic component can include a zeolite, an amorphous material, and/or a porous matrix. For example, the second catalytic component can include, but is not limited to, zeolite X, zeolite Y, USY, REY, RE-USY, MCM-9, MCM-22, MCM-41, SAPO-5, SAPO-37, SAPO-40, naturally occurring zeolites such as faujasite, mordenite, and the like, or any combination thereof. In another example, the second catalytic component can include boehmite, pseudoboehmite alumina, peptized pseudoboehmite alumina (PSA), alumina-containing gels, hydrotalcites, bauxite, and the like, or any combination thereof. In a further example, the second catalytic component can include one or more bottoms cracking additives such as BCMT™-500, BCMT™-500 LRT, BCMT™-DC, and BCMT™-MD, all commercially available from Albermarle Corporation, and BCA-105®, commercially available from the InterCat division Johnson Mathey Corporation. In at least one example, the second catalytic component can be zeolite Y and/or USY. In a specific example, the first catalytic component of the catalyst in line 120 can be ZSM-5 and the second catalytic component of the catalyst in line 120 can be zeolite Y.

The first catalytic component and/or the second catalytic component can be supported on, in, or otherwise about a support material, matrix, or binder. Illustrative support materials can include, but are not limited to, alumina, silica gel, and/or naturally occurring clays. The support material can be catalytically active or inactive. In one or more embodiments, the catalytically active support material, matrix, or binder can have a porous internal cell structure with an average pore size greater than about 6.4 angstroms (Å).

The first catalytic component and the second catalytic component can be deposited or supported on separate support material to provide mixed catalyst particles. In another example, the first catalytic component and the second catalytic component can be included on the same support material to provide homogenous catalyst particles. In another example, the first catalytic component can be supported by the second catalytic component. Said another way, either the first catalytic component or the second catalytic component can also serve the function of the support material for the other component. In one or more embodiments, the active support material, or active matrix, can include boehmite, pseudoboehmite alumina, peptized pseudoboehmite alumina (PSA), or alumina-containing gels.

The amount of the first catalytic component in the catalyst in line 120 can be at least 1 wt %, at least 2 wt %, at least 5 wt %, at least 10 wt %, at least 15 wt %, at least 20 wt %, at least 25 wt %, at least 30 wt %, at least 35 wt %, at least 40 wt %, at least 45 wt %, or at least 50 wt %, based on the combined weight of the first catalytic component and the second catalytic component. For example, the amount of the first catalytic component in the catalyst in line 120 can be from a low of about 0.1 wt %, about 1 wt %, about 4 wt %, about 8 wt %, or about 15 wt % to a high of about 20 wt %, about 30 wt %, about 40 wt %, about 50 wt %, or about 60 wt %, based on the combined weight of the first catalytic component and the larger poor catalytic component. The amount of the second catalytic component in the catalyst in line 120 can be at least 1 wt %, at least 2 wt %, at least 5 wt %, at least 10 wt %, at least 15 wt %, at least 20 wt %, at least 25 wt %, at least 30 wt %, at least 35 wt %, at least 40 wt %, at least 45 wt %, or at least 50 wt %, based on the combined weight of the first catalytic component and the second catalytic component. For example, the amount of the second component in the catalyst in line 120 can be from a low of about 0.1 wt %, about 2 wt %, about 10 wt %, about 25 wt %, or about 40 wt % to a high of about 50 wt %, about 60 wt %, about 70 wt %, about 80 wt %, or about 90 wt %, based on the combined weight of the first catalytic component and the larger pore catalytic component. The weight ratio of the first catalytic component to the second catalytic component can be from about 1:1000 to about 1000:1, from about 1:100 to about 100:1, from about 1:20 to about 20:1, from about 1:10 to about 10:1, from about 1:5 to about 5:1, from about 1:4 to about 4:1, from about 1:3 to about 3:1, from about 1:2 to about 2:1, or about 1:1.5 to about 1.5:1.

The amount of the first catalytic component in the catalyst in line 120 can be at least 1 wt %, at least 10 wt %, at least 20 wt %, at least 30 wt %, or at least 40 wt %, based on the total weight of the catalyst in line 120. As used herein, the term "total weight of the catalyst" includes both the weight of catalytic components and the weight of any noncatalytic/inert components of the catalyst. For example, the amount of the first component in the catalyst in line 120 can be from a low of about 1 wt %, about 5 wt %, about 10 wt %, about 20, about 30 wt %, or about 40 wt % to a high of about 45 wt %, about 50 wt %, about 55 wt %, about 60 wt %, about 65 wt %, or about 70 wt %, based on the total weight of the catalyst in line 120. The amount of the second catalytic component in the catalyst in line 120 can be at least 2 wt %, at least 15 wt %, at least 30 wt %, or at least 50 wt %, based on the total weight of the catalyst in line 120. For example, the amount of the second component in the catalyst in line 120 can be from a low of about 1 wt %, about 5 wt %, about 10 wt %, about 20 wt %, or about 30 wt % to a high of about 65 wt %, about 70 wt %, about 75 wt %, about 80 wt %, or about 95 wt %, based on the total weight of the catalyst in line 120.

The hydrocarbon or feed in line 104 can be or include any hydrocarbon having one or more carbon atoms. In one or more embodiments, the hydrocarbon in line 104 can be a light hydrocarbon limited to hydrocarbons having a carbon number less than 12. For example, the hydrocarbon in line 104 can include $C_2$-$C_{10}$ hydrocarbons. Examples of suitable hydrocarbons can include, but are not limited to, paraffinic, cycloparaffinic, monoolefinic, diolefinic, cycloolefinic, naphthenic, and aromatic hydrocarbons, and hydrocarbon oxygenates. Further representative examples of hydrocarbons can include light paraffinic naphtha; heavy paraffinic naphtha; light olefinic naphtha; heavy olefinic naphtha; mixed paraffinic C4s; mixed olefinic C4s (such as raffinates); diolefins (such as butadiene); mixed paraffinic C5s; mixed olefinic C5s (such as raffinates); mixed paraffinic and cycloparaffinic C6s; non-aromatic fractions from an aromatics extraction unit; oxygenate-containing products from a Fischer-Tropsch unit; or the like; or any combination thereof. Hydrocarbon oxygenates can include alcohols having carbon numbers of one to four, ethers having carbon numbers of two to eight and the like. Examples include methanol, ethanol, dimethyl ether, methyl tertiary butyl ether (MTBE), ethyl tertiary butyl ether, tertiary amyl methyl ether (TAME), tertiary amyl ethyl ether and the like.

As used herein, the term "light" in reference to feedstock or hydrocarbons generally refers to hydrocarbons having a carbon number less than or equal to 12 and optionally less than 10, and "heavy" refers to hydrocarbons having a carbon number greater than 12. In one or more embodiments, the light hydrocarbon can have a carbon number from 1 to 12, 1 to about 10, 1 to about 8, 1 to about 6, or 1 to about 4. In one or more embodiments, the light hydrocarbon can include one or more $C_2$-$C_8$ hydrocarbons or $C_2$-$C_{10}$ hydrocarbons, or hydrocarbons. As used herein, the term "carbon number" refers to the number of carbon atoms in a specific compound. The terms "naphtha" or "full range naphtha," as used herein, refers to a hydrocarbon mixture having a 10 percent point below 60° C. and a 95 percent point below 240° C. as determined by distillation in accordance with the standard method of ASTM-D86; "light naphtha" to a naphtha fraction with a boiling range within the range of $C_4$ to 166° C.; and "heavy naphtha" to a naphtha fraction with a boiling range within the range of 166° C. to 211° C. As used herein, the term "paraffinic" in reference to a feed or stream refers to a light hydrocarbon mixture including at least 80 weight percent paraffins, no more than 10 weight percent aromatics, and no more than 40 weight percent cycloparaffins. As used herein, the term "aromatic" in reference to a feed or stream refers to a light hydrocarbon mixture including more than 50 weight percent aromatics. As used herein, the term "olefinic" in reference to a feed or stream refers to a light hydrocarbon mixture including at least 20 weight percent olefins. As used herein, the term "mixed $C_4$'s" in reference to a feed or stream refers to a light hydrocarbon mixture including at least 90 weight percent of hydrocarbon compounds having 4 carbon atoms.

Hydrocarbon introduced via line 104 to the reaction riser 105 can include $C_2$-$C_{10}$ hydrocarbons in an amount from a low of about 20 wt %, about 30 wt %, or about 40 wt % to a high of about 80 wt %, about 90 wt %, or about 100 wt %. For example, the hydrocarbon in line 104 can have a $C_2$-$C_{10}$ hydrocarbon concentration from about 20 wt % to about 100 wt %, from about 30 wt % to about 99.9 wt %, from about 60 wt % to about 99 wt %, or from about 85 wt % to about 99 wt %, or from about 95 wt % to about 100 wt %. The hydrocarbon introduced via line 104 to the reaction riser 105 can include $C_4$-$C_8$ hydrocarbons in an amount from a low of about 10 wt %, about 20 wt %, or about 30 wt % to a high of about 70 wt %, about 80 wt %, or about 100 wt %. For example, the hydrocarbon in line 104 can have a $C_4$-$C_8$ hydrocarbon concentration from about 60 wt % to about 100 wt %, about 70 wt % to about 100 wt %, or about 90 wt % to about 100 wt %. The hydrocarbon introduced via line 104 to the reaction riser 105 can have less than about 50 wt %, about 20 wt %, about 10 wt %, about 5 wt %, about 1 wt %, about 0.1 wt %, or about 0.01 wt % $C_{11}$+ hydrocarbons. The hydrocarbon introduced via line 104 to the reaction riser 105 can have less than about 60 wt %, about 30 wt %, about 15 wt %, about 10 wt %, about 5 wt %, about 1 wt %, or about 0.1 wt % $C_9$+ hydrocarbons.

The hydrocarbon introduced via line 104 to the reaction riser 105 can include one or more olefins in an amount from a low of about 0 wt %, about 10 wt %, or about 20 wt % to a high of about 50 wt %, about 75 wt %, or about 100 wt %. For example, the hydrocarbon in line 104 can have an olefins concentration from about 0.1 wt % to about 99.9 wt %, about 10 wt % to about 75 wt %, or about 20 wt % to about 50 wt %. The hydrocarbon introduced via line 104 to the reaction riser 105 can include one or more $C_4$ olefins in an amount from a low of about 0 wt %, about 1 wt %, or about 10 wt % to a high of about 20 wt %, about 40 wt %, or about 100 wt %. For example, the hydrocarbon in line 104 can have a $C_4$ olefins concentration from about 0.1 wt % to about 99.9 wt %, about 1 wt % to about 30 wt %, or about 5 wt % to about 15 wt %. The hydrocarbon introduced via line 104 to the reaction riser 105 can include one or more dienes in an amount from a low of about 0 wt %, about 0.1 wt %, or about 1 wt % to a high of about 10 wt %, about 20 wt %, or about 40 wt %. For example, the hydrocarbon in line 104 can have a dienes concentration from about 0 wt % to about 25 wt %, about 0.1 wt % to about 10 wt %, or about 1 wt % to about 5 wt %. In one or more embodiments, the hydrocarbon introduced via line 104 to the reaction riser 105 can have less than about 40 wt %, about 10 wt %, about 1 wt %, or about 0.1 wt % dienes.

In one or more embodiments, the process can include partially hydrogenating a diolefin-rich stream to produce the hydrocarbons in line 104. For example, the hydrocarbons in line 104 can include mono-olefins and from about 0.05 wt % to about 20 wt % or from about 1 wt % to about 15 wt % diolefins.

The hydrocarbon in line 104 can be a byproduct or downstream product from the production of syngas. For example, the hydrocarbon in line 104 can have low concentrations of sulfur or other impurities. In one or more embodiments, the hydrocarbon in line 104 can have a concentration of sulfur and/or one or more sulfur compounds of less than about 1,000 parts per million by weight (ppmw), less than about 500 ppmw, less than about 100 ppmw, less than about 10 ppmw, or less than about 1 ppmw. In some embodiments, the hydrocarbon in line 104 can be sulfur-free or substantially free of sulfur. As used herein, the term "substantially free of sulfur" means the hydrocarbon in line 104 contain less than about 1 ppmw sulfur.

In one or more embodiments in a low sulfur feedstock application, sulfur, beyond the amount contained in the feedstock can be introduced to the reaction riser 105 to retard the rate of coke formation within the equipment. The sulfur introduced to the reaction riser 105 can be present in any sulfur containing compounds such as, for example, sulfides, organosulfur compounds, sulfur oxides, sulfonium compounds, and the like. For example, hydrogen sulfide, disulfides, sulfur dioxide, sulfones, sulfoxides, sulfonates, thiols, thioamides, thioesters, thioethers, or any combination thereof can be introduced to the reaction riser 105.

The sulfur containing compounds can be introduced to the reaction riser 105 in an amount from a low of about 1 ppmw, about 5 ppmw, about 20 ppmw, about 50 ppmw, about 100 ppmw, or about 200 ppmw to a high of about 300 ppmw, about 500 ppmw, about 700 ppmw, about 1,000 ppmw, about 1,500 ppmw, or about 2,000 ppmw based on the weight of the hydrocarbons introduced to the reaction riser 105. For example, the hydrocarbons in line 104 can have a sulfur and/or one or more sulfur compounds concentration from about 20 ppmw, about 50 ppmw, about 100 ppmw, or about 200 ppmw to a high of about 250 ppmw, about 400 ppmw, about 700 ppmw, or about 1,000 ppmw.

The sulfur containing compounds can be introduced to the reaction riser 105 at any location along the reaction riser 105. For example, the sulfur containing compounds can be introduced to the reaction riser 105 with the hydrocarbons in line 104. In another example, the sulfur containing compounds can be introduced to the reaction riser 105 separately from the hydrocarbons. For example, the sulfur containing compounds can be separately introduced to the reaction riser 105 at a location on the reaction riser 105 below, or upstream, where the hydrocarbons in line 104 enter the reaction riser 105. In another example, the sulfur containing compounds can be separately introduced to the reaction riser 105 at a location on the reaction riser 105 at or above, or downstream, where the hydrocarbons in line 104 enter the reaction riser 105.

Steam can also be used to retard the rate of coke formation in the reactor. Steam via line 125, the hydrocarbon via line 104, and one or more catalysts via line 120 can be introduced to the reaction riser 105, forming a fluidized mixture ("reaction mixture") therein. The steam via line 125 and the catalyst via line 120 can be introduced separately to the reaction riser 105. Alternatively, the steam and the catalyst can be mixed and introduced together as a mixture to the reaction riser 105. In another example, the steam and the hydrocarbon can be mixed and introduced together as a mixture to the reaction riser 105.

Heat in the reaction riser 105, provided by the steam via line 125 and the catalyst via line 120, can vaporize at least a portion of the hydrocarbon introduced via line 104, if not already vapor, to provide the reaction mixture therein. Supplemental heat can be provided to the reaction riser 105 using waste heat provided from the regenerator 115. Within the reaction riser 105, the hydrocarbons within the reaction mixture can be cracked to provide a riser effluent via the transfer line 110. At least a portion of the hydrocarbon by-products present in the reaction riser 105 can deposit on the surface of the catalyst particulates, forming coked-catalyst particulates or spent catalyst. Thus, the riser effluent exiting the reaction riser 105 can include coked-catalyst particulates, gaseous hydrocarbons, carbon dust or particulates, steam, and inerts.

The hydrocarbons introduced via line 104 to the reaction riser 105 can react in the presence of the first catalytic component in the reaction riser 105 to produce dienes. For example, hydrocarbons can react in the presence of the first catalytic component to produce dienes in an amount from a low of about 0.1 wt %, about 1 wt %, about 1.5 wt %, about 2 wt %, or about 3 wt % to a high of about 4 wt %, about 5 wt %, about 10 wt %, about 15 wt %, or about 20 wt % based on the weight of the hydrocarbons introduced from line 104 to the reaction riser 105.

The diolefins and/or other olefin containing compounds in the reaction riser 105 can form coke on the catalyst particles. The reaction conditions in the reaction riser 105 can cause the diene and/or other olefin containing compounds to undergo oligomerization, cyclization, and/or dehydrogenation in the second catalytic component of the catalyst particles. The diolefins and/or other olefin containing compounds can oligomerize, cyclize, and/or dehydrogenate to form coke on the catalyst. The second catalytic component of the catalyst can have any pore size capable of encouraging coke formation by the oligomerization, cyclization, and/or dehydrogenation of diolefins and olefin containing compounds on the catalyst.

The weight ratio of the amount of coke generated in the reaction riser 105 and deposited on the catalyst to the amount of hydrocarbons introduced to the reaction riser 105 can be from a low of about 0.001:1, about 0.002:1, about 0.005:1, about 0.008:1, about 0.01:1, or about 0.015:1 to a high of about 0.02:1, about 0.025:1, about 0.05:1, about 0.1:1, about 0.15:1, or about 0.25:1. For example, the weight ratio of the amount of coke generated in the reaction riser 105 and deposited on the catalyst to the amount of hydrocarbons introduced to the reaction riser 105 can be from about 0.001:1 to about 0.08:1, from about 0.01:1 to about 0.05:1, or from about 0.02:1 to about 0.04:1.

A coke precursor can be introduced to the riser reactor 105. The coke precursor can be fed to the riser reactor 105 at a ratio of from 1 to 40 parts by weight coke precursor to 100 parts by weight hydrocarbon feed in line 104. Illustrative coke precursors can include, but are not limited to, acetylene, alkyl- or allyl-substituted acetylene (such as methyl acetylene, vinyl acetylene, or the like), a diolefin (such as butadiene), vacuum gas oils, reduced crudes, atmospheric tower bottoms, vacuum tower bottoms, or any combination thereof. The coke precursor can also include an aromatic hydrocarbon or an aromatic precursor that forms aromatics in the reaction riser 105. The coke precursor can also include gas oil. The reaction riser 105 operating conditions with the coke precursor fed to the riser reactor 105 can include a higher temperature, higher catalyst-to-feed ratio, and/or lower hydrocarbon partial pressure.

The catalyst-to-hydrocarbon weight ratio can range from about 2:1 to about 35:1, from about 2:1 to about 30:1, from about 5:1 to about 25:1, from about 10:1 to about 20:1, or from about 15:1 to about 18:1. The reaction riser 105 can be operated at a temperature from a low of about 450° C., about 475° C., about 500° C., about 525° C., about 550° C., or about 575° C. to a high of about 635° C., about 655° C., about 675° C., about 700° C., about 750° C., or about 825° C. For example, the reaction riser 105 can be operated at a temperature from about 400° C. to about 675° C., from about 605° C. to about 670° C., from about 610° C. to about 660° C., or from about 615° C. to about 650° C. In at least one specific embodiment, the reaction riser 105 can be operated at a temperature of about 605° C., about 615° C., about 625° C., about 630° C., about 640° C., or about 650° C.

As used herein, reference to a riser temperature shall mean the temperature of the riser effluent exiting at the top of the riser. The thermal equilibrium of the riser feed can be lower than the riser exit temperature and the temperature can vary throughout the riser depending on the reactions.

The pressure in the reaction riser 105 can be from a low of about 40 kPa, about 55 kPa, about 65 kPa, or about 70 kPa to a high of about 650 kPa, about 675 kPa, about 700 kPa, or about 725 kPa. Other operating conditions can be as discussed and described in U.S. Pat. No. 7,128,827. In at least one specific embodiment, the hydrocarbon can be heated within the reaction riser 105 to a temperature of about 590° C. to about 675° C. at a pressure of about 68 kPa to about 690 kPa.

The velocity of the reaction mixture flowing through the reaction riser 105 can be from about 3 m/sec to about 27 m/sec, about 6 m/sec to about 25 m/sec, or about 9 m/sec to about 21 m/sec. The residence time of the reaction mixture in the reaction riser 105 can be less than about 20 seconds, less than about 10 seconds, less than about 8 seconds, less than about 4 seconds, or less than about 2 seconds.

Illustrative feeds, reactor units, and operating conditions are also discussed and described in U.S. Pat. Nos. 6,106,697; 7,011,740; 7,128,827; 7,153,479; 7,270,739; 7,435,331; 7,491,315; 7,611,622; and 7,820,033 and U.S. Pre-Grant Publication Nos. 2002/0003103; 2002/0189973; 2009/0299118; 2009/0299119; 2011/0251046; and 2012/0165591, which are incorporated by reference herein in their entirety.

The hydrocarbon in line 104 can be pre-heated prior to introduction to the reaction riser 105. Although not shown in FIG. 1, a regenerative heat exchanger using waste process heat can be used to pre-heat the light hydrocarbon feed introduced via line 104. The temperature of the hydrocarbon in line 104 can be from about 200° C. to about 500° C., about 300° C. to about 400° C., or about 350° C. to about 390° C. The pressure of the light hydrocarbon via line 104 can be from about 101 kPa to about 3,450 kPa, about 101 kPa to about 2,450 kPa, or about 101 kPa to about 700 kPa.

The hydrocarbon in line 104 can be partially or completely vaporized prior to introduction to the reaction riser 105. The amount of the hydrocarbon in line 104 that can be vaporized can range from a low of 0 vol %, about 5 vol %, about 10 vol %, about 20 vol %, about 30 vol %, or about 40 vol % to a high of about 70 vol %, about 80 vol %, about 90 vol %, or about 100 vol %. For example, the hydrocarbon in line 104 can be about 80 wt % or more vaporized, about 85 wt % or more vaporized, about 90 wt % or more vaporized, about 95 wt % or more vaporized, or about 99 wt % or more vaporized or completely vaporized prior to introduction to the reaction riser 105. In another example, the hydrocarbon in line 104 can be 100% vapor for 90% of the time. Within the reaction riser 105, the pressure and temperature can be adjusted either manually or automatically to compensate for variations in the composition of the hydrocarbon in line 104 and to maximize the yield of preferred hydrocarbons obtained in a cracked product recovered via line 135 by cracking the hydrocarbon in line 104 in the presence of the catalysts.

The steam introduced via line 125 to the reaction riser 105 can be saturated. The pressure of the saturated steam can be from about 101 kPa to about 6,000 kPa, about 500 kPa to about 6,000 kPa, or about 2,000 kPa to about 6,000 kPa. For example, the pressure of the saturated steam can range from about 101 kPa to about 8,300 kPa, about 101 kPa to about 4,000 kPa, or about 101 kPa to about 2,000 kPa.

The steam introduced via line 125 to the reaction riser 105 can be superheated. The pressure of the superheated steam can be from a low of about 100 kPa to a high of about 8,500 kPa. The pressure of the superheated steam via line 125 can range from about 100 kPa to about 8,300 kPa, about 100 kPa to about 4,000 kPa, or about 100 kPa to about 2,000 kPa. The temperature of the superheated steam via line 125 can be a minimum of about 200° C., about 230° C., about 260° C., or about 290° C.

The steam can optionally be introduced via line 125 to the reaction riser 105 at a rate proportionate to the hydrocarbon feed rate introduced via line 104. In one example, the steam-to-hydrocarbon weight ratio can range from about 1:10 to about 1:15 or about 1:5 to about 1:30. The steam-to-hydrocarbon weight ratio can remain constant or can vary.

The product mixture can flow, via the transfer line 110, to the separator 150, where the coked-catalyst particulates and/or other particulates can be separated from the gaseous hydrocarbons, steam, and inerts. The separator 150 can have a larger cross-sectional area than the reaction riser 105 and/or the transfer line 110, which reduces the velocity of the cracked product mixture, allowing the heavier coked-catalyst particulates and/or other particulates to separate from the gaseous hydrocarbons, steam, and inerts. In one or more embodiments, a steam purge (not shown) can be added to the separator 150 to assist in separating the gaseous hydrocarbons from the coked-catalyst particulates, i.e., stripping the gaseous hydrocarbons from the solids. In other words, the separator 150 can be a self-stripping separator, e.g., a self-stripping cyclone.

The gaseous hydrocarbons ("cracked product") via line 135 can be recovered from the separator 150. The product in line 135 can be further processed (not shown), such as by dehydrating or fractionating to provide one or more finished products including, but not limited to, one or more olefins, paraffins, aromatics, mixtures thereof, and/or combinations thereof. For example, the product via line 135 can be introduced to a quench tower (not shown) that quenches the product and separates entrained catalyst particulates therefrom. Entrained catalyst particulates separated from the cracked product can then be recycled back to the reaction riser 105 or to the regenerator 115. A suitable FCC system having a quench tower for quenching and separating entrained catalyst particulates from the riser effluent is discussed and described in U.S. Pat. No. 7,153,479 and/or U.S. Pat. No. 7,011,740, which is incorporated by reference herein.

The separator 150 can separate from a low of about 90%, about 90.5%, about 91%, or about 91.5% to a high of about 98%, about 99%, about 99.5%, or about 99.999% of the particulates from the cracked product mixture via the transfer line 110. For example, the separator 150 can separate of from about 90% to about 99.9%, about 95% to about 99%, or about 97.5% to about 99.999% of the particulates from the riser effluent via the transfer line 110.

The solids, i.e., coked-catalyst particulates, can free fall through the separator 150 and can be introduced via line 111 to the regenerator 115. Although not shown, at least a portion of the solids can be introduced to the regenerator after passing through a stripper. The coked-catalyst particulates introduced via line 111 can be combined with one or more fluids (not shown) within the regenerator 115 to provide a flue gas via line 117 and regenerated catalyst via line 120. The one or more fluids can include one or more oxidants and/or supplemental fuel. Illustrative oxidants can include, but are not limited to, air, oxygen, oxygen, oxygen-enriched air, ozone, hydrogen peroxide, an essentially nitrogen-free oxidant, or any combination thereof. As used herein, the term "essentially oxygen" refers to a fluid containing more than 50 vol % oxygen. As used herein, the term "oxygen-enriched air" refers to a fluid containing about 21 vol % oxygen to about 50 vol % oxygen. Oxygen-enriched air and/or essentially oxygen can be obtained, for example, from cryogenic distillation of air, pressure swing adsorption, membrane separation, or any combination thereof. As used herein, the term "essentially nitrogen-free," refers to an oxidant that contains about 5 vol % nitrogen or less, about 4 vol % nitrogen or less, about 3 vol % nitrogen or less, about 2 vol % nitrogen or less, or about 1 vol % nitrogen or less. The supplemental fuel can include any combustible material. For example, the supplemental fuel can include, but is not limited to, $C_1$ to $C_{20}$ hydrocarbons and/or carbon. The supplemental fuel can be introduced to the regenerator 115 as a liquid, gas, solid, or any combination thereof. The supplemental fuel can be introduced in a separate line from the oxidant. The oxidants can react with the carbonaceous matter on the coked-catalyst particulates to combust or otherwise burn the carbon ("coke") off the surface of the catalyst particulate. Should the supplemental fuel be introduced, the oxidants can react with the supplemental fuel to combust the supplemental fuel and generate heat. The removal of the coke from the surface of the catalyst particulates re-exposes the reactive surfaces of the catalyst particulates, thereby "regenerating" the catalyst particulates and permitting reuse thereof. Combustion by-products, such as carbon monoxide, nitrogen oxides, nitrogen oxide precursors, and carbon dioxide, can be removed from the regenerator 115 as a waste or flue gas via line 117. The regenerated catalyst particulates can be recovered via line 120, which can be recycled to the reaction riser 105. In one or more embodiments, fresh, unused, catalyst can be added (not shown) to the regenerator 115, the regenerated catalyst in line 120, and/or to the reaction riser 105.

The coked-catalyst particulates introduced via line 111 can be combined with one or more oxidants (not shown) within the regenerator 115 to provide a flue gas via line 117 and regenerated catalyst via line 120. In one or more embodiments, the oxidants can react with the carbonaceous matter on the coked-catalyst particulates to combust or otherwise burn the carbon ("coke") off the surface of the catalyst particulate without the need for supplemental fuel. For example, a flue gas via line 117 and regenerated catalyst via line 120 can be obtained from the regenerator 115 in the absence of supplemental fuel. In one or more embodiments, the coked catalyst particles obtained from using the larger pore catalytically active component can result in a reduction of supplemental fuel added to the regenerator. For example, the coked catalyst particles obtained from using the larger pore catalytically active component can result in a reduction of at least 5 wt %, at least 20 wt %, at least 50 wt %, or at least 80 wt % of the supplemental fuel added to the regenerator.

The regenerator 115 can be operated in full burn mode, partial burn mode, or anywhere in between. Operating the regenerator 115 in full burn mode can provide an exhaust gas or flue gas via line 117 that can contain a larger amount of nitrogen oxides ("NOx") and NOx precursors and a decreased amount of carbon monoxide (CO) relative to the partial burn mode. Operating the regenerator 115 in a partial burn mode can provide an exhaust gas or flue gas via line 117 that can contain a larger amount of CO and a lesser amount of NOx and NOx precursors relative to the full burn mode. Operating the regenerator 115 in between the two extremes of full burn and partial burn can provide an exhaust gas via line 117 that contains less NOx and NOx precursors and more CO when compared to the full burn mode. The NOx gases can include, but are not limited to, NO, $NO_2$, and $N_2O$. In another example, the NOx precursors can include, but are not limited to, HCN, $NH_3$, CN, and HNO.

The flue gas via line 117 can be introduced to one or more optional CO boilers (not shown) to remove additional CO. The one or more CO boilers can be any type of CO boiler. The CO boiler can be operated in multiple stages to reduce the flame temperature occurring in any one stage and limit NOx formation in an oxidizing atmosphere. Low NOx burners can also be used to burn a fuel gas (not shown) to keep the CO boiler lit. Ammonia or an ammonia precursor, such as urea, can be introduced (not shown) to the optional CO boiler to reduce NOx emissions even further. These materials can react quickly with NOx and NOx precursors to reduce it to nitrogen.

At least a portion of the flue gas via line 117 and/or flue gas from the optional CO boiler can be vented to the atmosphere and/or sent to one or more heat recovery units (not shown) and then vented to the atmosphere, sequestered underground, or otherwise disposed. The optional CO boiler, if used, can reduce the CO content of the flue gas via line 117 in an amount ranging from a low of about 5%, about 10%, about 15%, about 20% to a high of about 75%, about 80%, about 85%, or about 90%. For example, the optional CO boiler can reduce the CO content of the flue gas via line 117 by from about 5% to about 90%, from about 5% to about 75%, from about 5% to about 60%, or from about 5% to about 50%.

Although not shown, a carbon dioxide ($CO_2$) separation unit can be used to remove at least a portion of the CO, from the flue gas via line 117. CO, can be removed for sequestration or reuse, e.g., reuse through enhanced oil recovery.

The one or more optional heat recovery units (not shown) can include any device, system, or combination of systems and/or devices suitable for transferring heat from a fluid at a higher temperature to a fluid at a lower temperature. For example, the heat recovery unit can include, but is not limited to single or multiple pass heat exchange devices, such as shell and tube heat exchangers, plate and frame heat exchangers, spiral heat exchangers, bayonet type heat exchangers, U-tube heat exchangers, and/or any similar system or device.

A fluidized mixture containing spent catalyst particulates, regenerated catalyst particulates, oxidants, carbon monoxide, carbon dioxide, nitrogen oxides, and/or the fluid can be combined within the regenerator 115 with one or more optional doping agents introduced thereto (not shown). The dispersal and deposition of the doping agents on the regenerated catalyst can be enhanced by the high temperature and fluid velocity present in the regenerator 115. Although not shown, the optional doping agents can be mixed with a supplemental fuel, for example natural gas, and introduced to the regenerator 115.

The selection of an appropriate doping agent or additive or blend of two or more doping agents or additives can be based, at least in part, upon the composition of the incoming hydrocarbons in line 104, and/or desired gaseous hydrocarbons to be produced in the cracked product via line 135. For example, the addition of a class 2 doping agent such as magnesium or barium can preferentially increase the production of ethylene in the cracked product recovered via line 135. In another example, the addition of a class 13 doping agent, such as gallium, can result in increased production of aromatic hydrocarbons in the cracked product recovered via line 135. In yet another example, the addition of class 8, 9, or 10 doping agents such as ruthenium, rhodium, or palladium can preferentially increase the production of propylene in the cracked product recovered via line 135.

Doped catalyst particulates and/or regenerated catalyst particulates with or without one or more doping agents or additives can be recycled to the reaction riser 105 via line 120. The flow of regenerated catalyst particulates from the regenerator 115 can be controlled using one or more valves (not shown), which can be manually or automatically adjusted or controlled based upon parameters derived from process temperatures, pressures, flows, and/or other process conditions. About 90 wt % or more, about 95 wt % or more, about 99 wt % or more, or about 99.99 wt % or more of the regenerated catalyst particulates, makeup catalyst particulates, and/or doped catalyst particulates introduced via line 120 to the reaction riser 105 can be regenerated, optionally doped with one or more doping agents, and recycled via line 120 back to the reaction riser 105.

Although not shown, the particulate discharge section 153 of the separator 150 and/or line 111 can include one or more valves to manually or automatically adjust or control the flow of spent catalyst to the regenerator 115 based on parameters derived from process temperatures, pressures, flows, and/or other process conditions.

The cracked product can have an ethylene concentration of at least 1 wt %, at least 4 wt %, at least 8 wt %, or at least 12 wt %, based on the total weight of the cracked product. The cracked product can have a propylene concentration of at least 5 wt %, at least 10 wt %, at least 15 wt %, or at least 20 wt %, based on the total weight of the cracked product. The cracked product can have a dienes concentration of less than about 10 wt %, about 5 wt %, about 2 wt %, about 1 wt %, about 0.5 wt %, or about 0.1 wt %, based on the total weight of the cracked product. For example, the cracked product can have a dienes concentration from a low of about 0.001 wt %, about 0.01 wt %, about 0.1 wt %, about 0.2 wt %, or about 0.5 wt % to about 1 wt %, about 2 wt %, about 4 wt %, about 6 wt %, or about 8 wt % based on the total weight of the cracked product. The cracked product recovered via line 135 can have an olefins concentration of at least 10 wt %, at least 20 wt %, at least 40 wt %, or at least 50 wt %, based on the total weight of the cracked product. For example, the cracked product can have an olefins concentration from a low of about 5 wt %, about 10 wt %, about 15 wt %, about 20 wt %, or about 25 wt % to a high of about 30 wt %, about 35 wt %, about 40 wt %, about 45 wt %, or about 50 wt % based on the total weight of the cracked product.

In one or more embodiments, a C5+ fraction of the cracked product, or cracked gasoline product, can have an olefins concentration of less than about 40 wt %, about 30 wt %, about 20 wt %, about 10 wt %, about 5 wt % based on the total weight of the cracked gasoline product. For example, the cracked gasoline product can have an olefins concentration from a low of about 0.01 wt %, about 0.1 wt %, about 0.5 wt %, about 1 wt %, about 1.5 wt % to a high of about 2 wt %, about 2.5 wt %, about 3 wt %, about 3.5 wt %, about 4 wt %, or about 5 wt % based on the total weight of the cracked gasoline product. In one or more embodiments, a C5+ fraction of the cracked product, or cracked gasoline product, can have a dienes concentration of less than about 5 wt %, about 3 wt %, about 1 wt %, about 0.5 wt %, about 0.2 wt % based on the total weight of the cracked gasoline product. For example, the cracked gasoline product can have an dienes concentration from a low of about 0.01 wt %, about 0.1 wt %, about 0.3 wt %, about 0.5 wt %, about 1 wt % to a high of about 2 wt %, about 2.5 wt %, about 3 wt %, about 3.5 wt %, about 4 wt %, or about 5 wt % based on the total weight of the cracked gasoline product.

At least 5 wt %, at least 15 wt %, at least 25 wt %, or at least 35 wt % of the feed can be converted to ethylene, propylene, or a combination thereof. For example, a low of about 10 wt %, about 15 wt %, or about 20 wt % to a high of about 30 wt %, about 35 wt %, or about 40 wt % of the feed can be converted to ethylene, propylene, or a combination thereof. At least 1 wt %, at least 5 wt %, or at least 10 wt % of the feed can be converted to ethylene. For example, a low of about 2 wt %, about 4 wt %, or about 6 wt % to a high of about 10 wt %, about 12 wt %, or about 14 wt % of the feed can be converted to ethylene. At least 4 wt %, at least 10 wt %, or at least 20 wt % of the feed can be converted to propylene. For example, a low of about 5 wt %, about 10 wt %, or about 15 wt % to a high of about 20 wt %, about 25 wt %, or about 30 wt % of the feed can be converted to propylene.

The cracked product recovered via line 135 can have a combined propylene and ethylene yield of at least 15 wt %, at least 20 wt %, at least 25 wt %, or at least 30 wt %. The cracked product can have an ethylene yield of at least 1 wt %, at least 2 wt %, at least 4 wt %, or at least 6 wt %. The cracked product can have a propylene yield of at least 10 wt %, at least 15 wt %, at least 20 wt %, or at least 25 wt %.

In some embodiments, the cracked product can have low concentrations of sulfur or other impurities. In one or more embodiments, the cracked product can have a sulfur concentration of less than about 1,000 parts per million by weight (ppmw), less than about 500 ppmw, less than about 100 ppmw, less than about 10 ppm, less than about 1 ppmw, less than about 0.1 ppmw, or less than about 0.01 ppmw. In some embodiments, the cracked product can be sulfur-free or substantially free of sulfur. As used herein, the term "substantially free of sulfur" means the product contains less than about 0.01 ppmw sulfur.

In one or more embodiments, the FCC system can be a dual riser FCC system (not shown). The dual riser FCC system can include one or more first risers, one or more second risers, one or more catalyst separation or disengagement zones, and one or more catalyst regeneration zones. A first hydrocarbon can be introduced to the first riser under first-riser conditions to form a first effluent enriched in ethylene, propylene, naphtha or a combination thereof. A second hydrocarbon can be introduced to the second riser under second-riser conditions to form a second effluent enriched in ethylene, propylene, naphtha or a combination thereof. The first and second hydrocarbons can be different from one another. The first-riser and second-riser conditions can be independently selected to favor production of ethylene, propylene, naphtha or a combination thereof.

As used herein, the term "dual riser" is used to refer to fluidized bed reactors employing two or more risers. While operating complexity and mechanical design considerations can limit the dual riser unit to two risers as a practical matter, a dual riser unit can have three, four or even more risers.

The ethylene and/or propylene yields can be increased in a process that employs a single converter and dual risers, i.e., a dual riser fluid bed reactor, for example, with light hydrocarbons in the first riser and $C_4$+ olefins in the second riser. By use of the dual riser fluid bed reactor, light hydrocarbons can be converted to predominately ethylene and/or propylene in the first riser and $C_4$+ hydrocarbon byproducts can be recycled and converted to ethylene and/or propylene in the second riser. By segregating feeds to the risers, each feed can be processed at conditions that optimize olefin production. For different feeds, the appropriate riser conditions can be different. For example, with segregated paraffinic and olefinic hydrocarbon feeds, the riser receiving the paraffinic feed can have a different temperature, catalyst-to-feed ratio, partial pressure, residence time, flow rate, catalyst, and/or other different process conditions as compared to the riser to which the olefinic feed is supplied.

The first hydrocarbons can be or include any hydrocarbon having one or more carbon atoms. The first hydrocarbon feed, or first hydrocarbon, can be a light hydrocarbon limited to hydrocarbons having a carbon number less than 12. For example, the first hydrocarbon in can include $C_2$-$C_{10}$ hydrocarbons. Examples of suitable hydrocarbons can include, but are not limited to, paraffinic, cycloparaffinic, monoolefinic, diolefinic, cycloolefinic, naphthenic, and aromatic hydrocarbons, and hydrocarbon oxygenates. Further representative examples of hydrocarbons can include light paraffinic naphtha; heavy paraffinic naphtha; light olefinic naphtha; heavy olefinic naphtha; mixed paraffinic C4s; mixed olefinic C4s (such as raffinates); diolefins (such as butadiene); mixed paraffinic C5s; mixed olefinic C5s (such as raffinates); mixed paraffinic and cycloparaffinic C6s; non-aromatic fractions from an aromatics extraction unit; oxygenate-containing products from a Fischer-Tropsch unit; or the like; or any combination thereof. Hydrocarbon oxygenates can include alcohols having carbon numbers ranging of one to four, ethers having carbon numbers of two to eight and the like. Examples include methanol, ethanol, dimethyl ether, methyl tertiary butyl ether (MTBE), ethyl tertiary butyl ether, tertiary amyl methyl ether (TAME), tertiary amyl ethyl ether and the like.

The second hydrocarbons can be the same or different from the first hydrocarbons. For example, the second hydrocarbons can be or include any olefinic feed having four or more carbon atoms. The second hydrocarbons can have a concentration of $C_4$+ olefins from a low of about 5 wt %, about 25 wt %, or about 40 wt % to a high of about 60 wt %, about 75 wt %, or about 99 wt %. For example, the second hydrocarbons can have a $C_4$+ olefins concentration from about 1 wt % to about 99 wt %, about 5 wt % to about 95 wt %, about 15 wt % to about 85 wt %, or about 25 wt % to about 75 wt %. The second hydrocarbons can contain dienes in any amount. The second hydrocarbons can contain dienes in an amount from a low of 0 wt %, about 1 wt %, or about 5 wt % to a high of about 10 wt %, about 20 wt %, or about 40 wt %. For example, the second hydrocarbons can have a dienes concentration from about 5 wt % to about 20 wt %, about 8 wt % to about 15 wt %, or about 10 wt % to about 12 wt %.

Hydrocarbons introduced to the first riser can include $C_2$-$C_{10}$ hydrocarbons in an amount from a low of about 50 wt %, about 75 wt %, or about 80 wt % to a high of about 90 wt %, about 95 wt %, or 100 wt %. For example, the hydrocarbons introduced to the first riser can have a $C_2$-$C_{10}$ hydrocarbons concentration from about 60 wt % to 100 wt %, about 80 wt % to about 99 wt %, or about 95 wt % to about 99 wt %. The hydrocarbons introduced to the first riser can include $C_4$-$C_8$ hydrocarbons in an amount from a low of about 80 wt %, about 85 wt %, or about 90 wt % to a high of about 95 wt %, about 99 wt %, or 100 wt %. For example, the hydrocarbons introduced to the first riser can have a $C_4$-$C_8$ hydrocarbons concentration from about 80 wt % to 100 wt %, about 85 wt % to about 99 wt %, or about 90 wt % to about 95 wt %. The hydrocarbons introduced to the first riser can have less than about 5 wt %, about 4 wt %, about 3 wt %, about 2 wt %, or about 1 wt % $C_{11}$+ hydrocarbons. The hydrocarbons introduced to the first riser can have less than about 10 wt %, about 5 wt %, about 3 wt %, about 2 wt %, or about 1 wt % $C_9$+ hydrocarbons.

The hydrocarbons introduced to the second riser can include the same or different hydrocarbons as the hydrocarbons introduced to the first riser. The hydrocarbons introduced to the second riser can also include one or more olefins in an amount from a low of about 20 wt %, about 30 wt %, or about 50 wt % to a high of about 75 wt %, about 90 wt %, or 100 wt %. For example, the hydrocarbons introduced to the second riser can have an olefins concentration from about 50 wt % to about 99 wt %, about 75 wt % to about 95 wt %, or about 80 wt % to about 95 wt %. The hydrocarbons introduced to the second riser can include one or more dienes in an amount from a low of about 1 wt %, about 2 wt %, or about 5 wt % to a high of about 10 wt %, about 15 wt %, or about 20 wt %. For example, the hydrocarbons introduced to the second riser can have a dienes concentration from about 5 wt % to about 20 wt %, about 8 wt % to about 15 wt %, or about 5 wt % to about 10 wt %. The hydrocarbons introduced to the second riser can include one or more $C_4$ olefins in an amount from a low of about 1 wt %, about 25 wt %, or about 50 wt % to a high of about 90 wt %, about 95 wt %, or 100 wt %. For example, the hydrocarbons introduced to the second riser can have a $C_4$ olefins concentration from about 1 wt % to about 95 wt %, about 25 wt % to about 90 wt %, or about 60 wt % to about 80 wt %.

The first and second hydrocarbons can be byproducts or downstream products from the production of syngas. For example, the first and second hydrocarbons can have low concentrations of sulfur or other impurities. In one or more embodiments, the first and second hydrocarbons can have a concentration of sulfur and/or one or more sulfur compounds of less than about 1,000 parts per million by weight (ppmw), less than about 500 ppmw, less than about 100 ppmw, less than about 10 ppmw, less than about 1 ppmw, less than about 0.1 ppmw, or less than 0.01 ppmw. In some embodiments, the first and second hydrocarbons can be sulfur-free or substantially free of sulfur. As used herein, the term "substantially free of sulfur" means the hydrocarbons contain less than about 0.01 ppmw sulfur.

The first riser and the second riser can include the same or different catalysts. In certain optional embodiments, both the first riser and the second riser can employ catalysts as described herein, either alone or in combination with one or more other catalysts. When other catalysts are used, such other catalysts can be present in only the first riser, only the second riser, or in both the first riser and the second riser, and when used in both the first riser and the second riser the additional catalysts can be the same or different. The catalyst particles can include smaller pore components and larger pore components as described herein. For example, the catalyst particles can include ZSM-5 and zeolite Y catalysts in any combination. In one or more embodiments, both of the first and second risers can employ a smaller pore component and/or a larger pore component. For example, both of the first and second risers can employ a catalyst containing ZSM-5. In an example, both of the first and second risers can employ a catalyst containing zeolite Y or USY. In one or more embodiments, both of the first and second risers can employ a catalyst having an active support material, such as for example, boehmite, pseudoboehmite alumina, peptized pseudoboehmite alumina (PSA), or alumina-containing gels. In an example, the both of the first and second risers can employ ZSM-5 and zeolite Y and/or USY. In another example, both of the first and second risers can employ ZSM-5 supported on an active matrix.

The first hydrocarbon and the second hydrocarbon can be introduced to the first riser and the second riser, respectively, at a first hydrocarbon to second hydrocarbon weight ratio from a low of about 1:10, about 1:5, about 1:4, about 1:3, about 1:2 to a high of about 2:1, about 3:1, about 4:1, about 5:1, about 10:1. For example, the first hydrocarbon to second hydrocarbon weight ratio can be from about 1:5 to about 5:1, from about 1:2 to about 2:1, from about 2:3 to about 3:2, from about 4:5 to about 5:4, or about 1:1.

The catalyst to first hydrocarbon weight ratio within the first riser and/or the second riser can be from about 2:1 to about 35:1, from about 2:1 to about 30:1, from about 5:1 to about 25:1, from about 10:1 to about 20:1, or from about 15:1 to about 18:1. The first riser and/or the second riser can be operated at a temperature ranging from a low of about 450° C., about 475° C., about 500° C., about 525° C., about 550° C., or about 575° C. to a high of about 635° C., about 655° C., about 675° C., about 700° C., about 750° C., or about 825° C. For example, the first riser and/or the second riser can be operated at a temperature ranging from about 400° C. to about 675° C., from about 605° C. to about 670° C., from about 610° C. to about 660° C., or from about 615° C. to about 650° C. In at least one specific embodiment, the first riser and/or the second riser can be operated at a temperature of about 605° C., about 615° C., about 625° C., about 630° C., about 640° C., or about 650° C.

The pressure in the first riser and/or the second riser can range from a low of about 40 kPa, about 55 kPa, about 65 kPa, or about 70 kPa to a high of about 650 kPa, about 675 kPa, about 700 kPa, or about 725 kPa. In one specific embodiment, cracking can occur at a temperature of from about 590° C. to about 675° C. and at a pressure of from about 68 kPa to about 690 kPa.

The catalytic cracking processes can include contacting the catalyst directly with the hydrocarbon feeds, forming a catalytically cracked product containing cracked hydrocarbons and coked catalyst. The coked catalyst can be separated from the catalytically cracked product within the disengagement zone. A substantial amount of the hydrocarbon that remains with the separated coked catalyst can be removed. The coked catalyst can be introduced to the catalyst regeneration zone or catalyst regenerator where at least a portion of the carbon or coke contained on/in the catalyst can be combusted to produce heat and regenerated catalyst. The regenerated catalyst can be recycled to the first riser and/or the second riser.

In an embodiment, the process can include preparing the first and/or second hydrocarbons by partially hydrogenating a diolefin-rich stream to obtain the first and/or second hydrocarbons. As an example, the second hydrocarbons can include mono-olefins and from 0.05 to 20 or from 1 to 15 weight percent diolefins. The diolefins or other diene containing compounds in the second riser can form coke on the catalyst particles disclosed herein. The reaction conditions in the second riser can cause the diene containing compounds to oligomerize in the larger pore catalytic component of the catalyst particles. The diolefins or other diene containing compounds can oligomerize to form coke on the catalyst. The larger pore catalytic component of the catalyst can have any pore size capable of encouraging coke formation by the oligomerization of diolefins or other diene containing compounds on the catalyst.

The weight ratio of the amount of coke generated in the first and/or second risers, to the amount of hydrocarbons introduced to the first and/or second risers can be from a low of about 0.001:1, about 0.002:1, about 0.005:1, about 0.008:1, about 0.01:1, or about 0.015:1 to a high of about 0.02:1, about 0.025:1, about 0.05:1, about 0.1:1, about 0.15:1, or about 0.25:1. For example, the weight ratio of the amount of coke generated in the first and/or second risers to the amount of hydrocarbons introduced to the first and/or second risers can be from about 0.001:1 to about 0.08:1, from about 0.01:1 to about 0.05:1, or from about 0.02:1 to about 0.04:1.

A coke precursor can be fed to the first and/or second risers. The coke precursor can be fed to the first and/or second risers at a ratio of from 1 to 40 parts by weight coke precursor to 100 parts by weight hydrocarbon feed. The coke precursor can include acetylene, alkyl- or allyl-substituted acetylene, (such as methyl acetylene, vinyl acetylene, or the like), a diolefin (such as butadiene), vacuum gas oils, reduced crudes, atmospheric tower bottoms, vacuum tower bottoms, or any combination thereof. The coke precursor can also include an aromatic hydrocarbon or an aromatic precursor that forms aromatics in the first and/or second risers. The coke precursor can also include gas oil. The first and/or second risers operating conditions with the coke precursor fed to the first and/or second risers can include a higher temperature, higher catalyst-to-feed ratio, and/or lower hydrocarbon partial pressure.

The amount of coke or carbon deposited on the catalyst particulates in the first riser and/or the second riser can range from a low of about 0.1 wt %, about 0.5 wt %, about 1 wt %, or about 2 wt % to a high of about 3 wt %, about 5 wt %, about 7.5 wt %, or about 10 wt %. For example, the amount of coke deposited on the catalyst particulates can range from about 1 wt % to about 10 wt %, from about 2 wt % to about 7.5 wt %, or from about 3 wt % to about 5 wt % based on the total weight of the carbon deposits and the catalyst particulates. In at least one specific embodiment, the amount of coke deposited on the catalyst particulates can be about 3 wt %.

The process can further include recovering catalyst and separating gas from the first and second effluents, optionally in a common separation device such as the separation zone. The recovered catalyst can be regenerated from the first riser and the second riser by combustion of coke in a regenerator, or regeneration zone, to obtain hot, regenerated catalyst. The hot regenerated catalyst can be re-circulated to the first and second risers to sustain a continuous operating mode. In one or more embodiments, $C_4+$ products can be recycled to the second riser to extinction, thus eliminating the need for a purge or "drag" stream to remove paraffins from the system.

The first and second effluents can be combined, or mixed. The combined effluent can contain the first effluent in an amount from a low about 1 wt %, about 10 wt %, about 20 wt %, about 30 wt %, or about 40 wt % to about 60 wt %, about 70 wt %, about 80 wt %, about 90 wt %, or about 99 wt %. For example, the combined effluent can contain the first effluent in amounts ranging from about 20 wt % to 80 wt %, about 30 wt % to about 70 wt %, about 40 wt % to about 60 wt %, or about 45 wt % to about 55 wt %. The combined effluent can contain the second effluent in amounts ranging from a low about 1 wt %, about 10 wt %, about 20 wt %, about 30 wt %, or about 40 wt % to about 60 wt %, about 70 wt %, about 80 wt %, about 90 wt %, or about 99 wt %. For example, the combined effluent can contain the second effluent in amounts ranging from about 20 wt % to 80 wt %, about 30 wt % to about 70 wt %, about 40 wt % to about 60 wt %, or about 45 wt % to about 55 wt %.

The first effluent can have an olefins concentration of at least 10 wt %, at least 25 wt %, at least 45 wt %, or at least 60 wt %, based on the total weight of the first effluent. The first effluent can have an ethylene concentration of at least 2 wt %, at least 4 wt %, at least 8 wt %, or at least 10 wt %, based on the total weight of the first effluent. The first effluent can have a propylene concentration of at least 4 wt %, at least 10 wt %, at least 20 wt %, or at least 30 wt %, based on the total weight of the first effluent. The first effluent can have a dienes concentration of at least 0.5 wt %, at least 1 wt %, at least 2 wt %, or at least 5 wt %, based on the total weight of the first effluent.

The second effluent can have an olefins concentration of at least 5 wt %, at least 10 wt %, at least 20 wt %, or at least 30 wt %, based on the total weight of the second effluent. The second effluent can have an ethylene concentration of at least 1 wt %, at least 2 wt %, at least 3 wt %, or at least 5 wt %, based on the total weight of the second effluent. The second effluent can have a propylene concentration of at least 2 wt %, at least 5 wt %, at least 10 wt %, or at least 20 wt %, based on the total weight of the second effluent. The second effluent can have a dienes concentration of at least 2 wt %, at least 2.5 wt %, at least 3 wt %, or at least 4 wt %, based on the total weight of the second effluent.

EXAMPLES

To provide a better understanding of the foregoing discussion, the following non-limiting examples are provided. All parts, proportions and percentages are by weight unless otherwise indicated.

The pilot plant used in this example included a FCC unit having cracking, stripping, and regeneration sections that were all operated under pressure with a continuous circulation of catalyst between the sections. A light hydrocarbon feed was pre-heated and introduced into the FCC unit. The combined stream was pre-heated to a temperature in the range from 150° F. to 700° F. and then atomized into a flowing catalyst stream. Regenerated catalyst at a temperature from 1050° F. to 1500° F. was passed through a slide valve that controlled the catalyst circulation rate to about 20 to 50 lb/hr and was transported via a short transfer line to the bottom of the riser with a flow of nitrogen. The feed stream and the catalyst stream were then mixed and transported to the riser.

Product vapors exited the riser at temperatures from 900° F. to 1200° F. and entered the stripper where catalyst was disengaged from the product vapors by cyclonic forces. The disengaged catalyst particles passed downward into the stripping section. A bed of spent catalyst was contacted with nitrogen in the stripping section. The stripping rates were set at the molar equivalent of over 6 pounds of $H_2O$ per 1,000 pounds of catalyst. The catalyst then flowed to the regenerator where coke was burned off. The regenerator controlled the level of carbon on regenerated catalyst. By adjusting the regenerator temperature and maintaining oxygen content of the flue gas exiting the regenerator between about 6 and 12 percent, carbon on regenerated catalyst levels below 0.10 weight percent were produced, with no significant production of CO in the flue gas.

Upon leaving the regenerator, the regenerator flue gas was cooled to about 10° C. to condense water of combustion. The remaining gas was then measured, analyzed, and vented. It was from these flue gas measurements that coke make was calculated. From the stripper, the product vapors were partially condensed in two stages of cooling. The liquid products were collected hourly. The uncondensed product gas was analyzed by an on-line gas chromatograph.

Table 1 shows the properties of a C4 Blend feed, a light hydrocarbon feed that was introduced to the riser.

TABLE 1

|  | Wt % | MW | Mol | mol % | Specific Gravity |
|---|---|---|---|---|---|
| n-butane | 10 | 58.12 | 581.2 | 10.23708 | 0.5844 |
| iso-butane | 23 | 58.123 | 1,336.83 | 23.5465 | 0.5631 |
| trans-2-butene | — | 56.11 | — | 0 | 0.5631 |
| 1-butene | 67 | 56.11 | 3,759.37 | 66.21641 | 0.609 |
| Total | 100 |  | 5,677.40 |  |  |
| Specific Gravity | 0.596 |  |  |  |  |
| API | 105.9229 |  |  |  |  |

Table 2 compares overall material balances for the riser using only a medium pore catalyst component and the riser using both medium pore and large pore catalyst components simultaneously. Example 1 utilized a single riser catalytic cracker using both a ZSM-5 catalyst and a zeolite Y catalyst and operated under an average temperature of about 1172° F. with a catalyst-to-hydrocarbon ratio of about 16.8. Example 2 utilized a single riser catalytic cracker using only a ZSM-5 catalyst and operated under an average temperature of about 1167° F. with a catalyst-to-hydrocarbon ratio of about 16.2. The results show that the use of a mixed catalyst, having a large pore catalytically active component and a medium pore catalytically active component, resulted in an over 400% increase by weight in coke production and about a 40% reduction by weight of ethylene.

TABLE 2

| Example Number | 1 | 2 |
|---|---|---|
| Start Time | 7:30 | 8:30 |
| End Time | 9:30 | 10:30 |
| ZSM-5 content of catalyst, wt. % | 8 | 10 |
| Feed | C4 blend | C4 Blend |
| Catalyst | Y zeolite FCC equilibrium catalyst and ZSM-5 Additive | ZSM-5 Additive |
| Riser length, ft. | Short | Short |
| Wt. % of feed recovered as product | 97.82 | 99.62 |
| Operating Conditions |  |  |
| Riser Outlet Temperature, ° F. | 1180 | 1159 |
| Riser Average Temperature, ° F. | 1172 | 1167 |
| Riser Outlet Pressure, psig | 34.7 | 35.0 |
| Oil Preheat Temperature, ° F. | 325 | 324 |
| Catalyst Inlet Temperature, ° F. | 1250 | 1249 |
| Mix Zone Temperature, ° F. | 1131 | 1131 |
| Oil Feed Rate, gms/hr | 1010 | 1021 |
| Catalyst Circulation Rate, lbs/hr | 37.50 | 36.50 |
| Cat/Oil ratio | 16.84 | 16.22 |
| Yields, weight % |  |  |
| C2 and lighter | 9.52 | 15.68 |
| C3's | 23.81 | 27.69 |
| C4's | 33.82 | 27.14 |
| C5-430° F. Gasoline | 26.52 | 27.45 |
| 430° F.-650° F. Cycle Oil | 2.8 | 0.3 |
| 650° F.+ Slurry | 0.94 | 0.3 |
| Coke | 2.59 | 0.51 |
| Total | 100.00 | 100.00 |
| Light ends, weight % |  |  |
| Hydrogen | 0.10 | 0.18 |
| Methane | 2.08 | 3.15 |
| Ethylene | 6.42 | 10.61 |
| Ethane | 0.92 | 1.73 |
| Propylene | 22.27 | 24.54 |
| Propane | 1.54 | 3.14 |

Table 3 shows properties of the G0579 catalyst, a partially rare earth exchanged USY catalyst, used in Example 1.

TABLE 3

| MAT (micro activity test) | wt % | 72 |
|---|---|---|
| Gas Factor |  | 1.7 |
| Coke Factor |  | 1 |
| Total Surface Area | m²/g | 194 |
| Matrix Surface Area | m²/g | 59 |
| Unit Cell Size | Angstroms | 24.24 |
| Ni* | ppmw | 135 |
| V* | ppmw | 287 |
| Na* | wt % | 0.27 |
| Cu | ppmw | 21 |
| Fe | wt % | 0.51 |
| Carbon | wt % | 0.07 |
| Sb | ppmw |  |
| $Re_2O_3$ | wt % | 0.31 |
| $Al_2O_3$ | wt % | 39.7 |
| Bulk Density | g/cc | 0.76 |
| Average Particle Size | microns | 64 |

Selected component concentrations in the liquid products from the condensed product vapors are listed in Table 4. The data shows that Example 1, which utilized both large and medium pore, or smaller pore, catalytically active components, achieved about a 45% reduction by weight of total diene concentration and a 28% reduction by weight of total olefin concentration when compared to Example 2, having the medium pore catalytically active components and not the large pore catalytically active components.

TABLE 4

|  | Example 1 | | Example 2 | |
|---|---|---|---|---|
| Liquid Fraction Component | Retention time | Weight % | Retention time | Weight % |
| Propylene | 7.478 | 0.115 | 7.48 | 0.363 |
| i-Butane | 7.962 | 0.153 | 7.955 | 0.000 |
| Butene-1 | 8.222 | 0.454 | 8.224 | 0.598 |
| n-Butane | 8.35 | 0.555 | 8.352 | 0.604 |
| t-Butene-2 | 8.485 | 0.286 | 8.488 | 0.338 |
| c-Butene-2 | 8.708 | 0.272 | 8.71 | 0.317 |
| i-Pentane | 9.778 | 0.29 | 9.781 | 0.091 |
| 2-Methylbutene-1 | 10.397 | 0.163 | 10.4 | 0.17 |
| n-Pentane | 10.553 | 0.088 | 10.556 | 0.059 |
| Isoprene | 10.724 | 0.081 | 10.727 | 0.133 |
| t-Pentene-2 | 10.81 | 0.164 | 10.813 | 0.17 |

TABLE 4-continued

|  | Example 1 | | Example 2 | |
| --- | --- | --- | --- | --- |
| Liquid Fraction Component | Retention time | Weight % | Retention time | Weight % |
| c-Pentene-2 | 11.11 | 0.099 | 11.113 | 0.103 |
| 2-Methylbutene-2 | 11.304 | 0.343 | 11.307 | 0.348 |
| 1t,3-Pentadiene | 11.41 | 0.09 | 11.413 | 0.135 |
| Cyclopentadiene | 11.924 | 0.228 | 11.926 | 0.463 |
| Cyclopentene | 12.93 | 0.153 | 12.934 | 0.236 |
| Cyclopentane | 13.55 | 0.11 | 13.553 | 0.128 |
| 2,3-Dimethylbutane | 13.624 | 0.041 | 13.623 | 0.000 |
| 4-Methyl-c-pentene-2 | 13.841 | 0.111 | 13.846 | 0.026 |
| 2-Methylpentene-1 | 14.972 | 0.05 | 14.976 | 0.05 |
| n-Hexane | 15.798 | 0.035 | 15.802 | 0.02 |
| c-Hexene-3 | 16.133 | 0.054 | 16.138 | 0.051 |
| t-Hexene-2 | 16.313 | 0.000 | 16.307 | 0.066 |
| 2-Methylpentene-2 | 16.506 | 0.000 | 16.499 | 0.093 |
| 3-Methylcyclopentene | 16.558 | 0.000 | 16.558 | 0.041 |
| 4,4-Dimethyl-t-pentene-2 | 17.784 | 0.001 | 17.786 | 0.001 |
| Methylcyclopentane | 17.911 | 0.224 | 17.917 | 0.204 |
| 2,3,3-Trimethylbutene-1 | 18.568 | 0.294 | 18.574 | 0.486 |
| 2,2,3-Trimethylbutane | 18.915 | 0.25 | 18.922 | 0.413 |
| 1-Methylcyclopentene | 20.008 | 0.292 | 20.016 | 0.352 |
| Benzene | 20.194 | 6.705 | 20.263 | 14.607 |
| 2-Methyl-t-hexene-3 | 21.422 | 0.13 | 21.433 | 0.216 |
| 4-Methyl-t/c-hexene-2 | 23.14 | 0.000 | 22.94 | 0.119 |
| Cyclohexene | 23.964 | 0.042 | 23.973 | 0.029 |
| Heptene-1 | 26.312 | 0.112 | 26.312 | 0.000 |
| 2-Ethylpentene-1 | 26.561 | 0.138 | 26.571 | 0.12 |
| 2-Methyl-2-hexene | 28.082 | 0.041 | 28.101 | 0.034 |
| 2,3,4-Trimethylpentane | 35.305 | 0.102 | 35.338 | 0.114 |
| Toluene | 36.36 | 28.667 | 36.439 | 35.525 |
| 1,1,2-Trimethylcyclopentane | 38.016 | 0.000 | 38.016 | 0.063 |
| Ethylbenzene | 55.94 | 1.867 | 55.968 | 2.315 |
| m-Xylene | 58.798 | 15.886 | 58.749 | 10.889 |
| p-Xylene | 59.042 | 5.819 | 59.052 | 7.711 |
| Styrene | 62.996 | 0.806 | 63.013 | 1.297 |
| o-Xylene | 64.279 | 6.82 | 64.202 | 3.773 |
| n-Propylbenzene | 76.058 | 0.148 | 76.064 | 0.185 |
| 1-Methyl-3-ethylbenzene | 77.344 | 1.817 | 77.335 | 1.279 |
| 1-Methyl-4-ethylbenzene | 77.61 | 0.71 | 77.614 | 0.773 |
| 1,3,5-Trimethylbenzene | 78.555 | 2.551 | 78.496 | 0.742 |
| 1-Methyl-2-ethylbenzene | 79.842 | 0.606 | 79.842 | 0.438 |
| 3-Ethyl-2-methylheptene-2 | 80.864 | 0.003 | 81.698 | 0.689 |
| 1,2,4-Trimethylbenzene | 81.754 | 0.708 | 81.816 | 0.000 |
| t-Butylbenzene | 82.126 | 7.644 | 82.034 | 2.893 |
| 1,2,3-Trimethylbenzene | 85.496 | 1.323 | 85.471 | 0.527 |
| 2,3-Dihydroindene | 86.792 | 0.109 | 86.796 | 0.187 |
| 1-Methyl-2-i-propylbenzene | 87.541 | 0.603 | 87.56 | 1.028 |
| 1,3-Diethylbenzene | 88.942 | 0.072 | 88.946 | 0.07 |
| 1-Methyl-3-n-propylbenzene | 89.233 | 0.143 | 89.236 | 0.113 |
| 1,4-Diethylbenzene | 89.652 | 0.109 | 89.652 | 0.000 |
| n-Butylbenzene | 90.017 | 0.479 | 90.014 | 0.239 |
| 1,4-Dimethyl-2-ethylbenzene | 92.048 | 0.264 | 92.049 | 0.174 |
| 1,3-Dimethyl-4-ethylbenzene | 92.232 | 0.309 | 92.236 | 0.224 |
| 1,2-Dimethyl-4-ethylbenzene | 92.875 | 0.442 | 92.873 | 0.267 |
| 1,2-Dimethyl-3-ethylbenzene | 94.921 | 0.099 | 94.926 | 0.064 |
| 1-Ethyl-4-i-propylbenzene | 96.146 | 0.623 | 96.14 | 0.301 |
| 1,2,4,5-Tetramethylbenzene | 96.496 | 0.863 | 96.484 | 0.387 |
| 5-Methylindan | 98.096 | 0.149 | 98.101 | 0.163 |
| 4-Methylindan | 98.836 | 0.525 | 98.846 | 0.743 |
| 2-Methylindan | 99.263 | 0.351 | 99.27 | 0.549 |
| 1-Methyl-3-n-butylbenzene | 99.457 | 0.423 | 99.463 | 0.32 |
| s-Pentylbenzene | 99.757 | 0.009 | 99.762 | 0.016 |
| Naphthalene | 101.795 | 2.013 | 101.781 | 1.388 |
| 1-t-Butyl-3,5-dimethylbenzene | 102.244 | 0.022 | 102.242 | 0.000 |
| 1,3-Di-n-propylbenzene | 104.521 | 0.038 | 104.525 | 0.034 |
| 1-Methylnaphthalene | 111.187 | 2.853 | 111.149 | 1.413 |
| Total Dienes |  | 0.399 |  | 0.731 |
| Total Olefins |  | 3.037 |  | 4.596 |
| C5+ Olefins |  | 1.910 |  | 2.980 |
| C7+ Olefins |  | 0.741 |  | 1.606 |
| C10+ Olefins |  | 0.003 |  | 0.707 |

The example shows that utilizing a medium pore catalytically active component and a large pore catalytically active component together in a riser can significantly increase the amount of coke deposited on the catalyst while reducing the amounts of dienes and olefins in a gasoline product. The increased presence of coke on the catalyst together with the reduced dienes and other olefins in the product indicates that the amount of coke precursors, such as dienes and other olefins, in the hydrocarbon mixture in the riser has been reduced through the process of coke formation on the catalyst. Thus, the increased coke on the catalyst particles and the reduced dienes and olefins results in a reduced formation of coke on the downstream FCC processing equipment including the ducts or transfer lines 110 and the separators 150. Also, the increased coke deposited on the catalyst can be burned in the regenerator 115, providing heat to the reaction in the reaction riser 105. The heat produced by burning the increased coke on the catalyst can also reduce or eliminate the need for a supplemental fuel supply to the regenerator 115. Additionally, the reduced concentration of dienes and olefins in the product provides the referenced improvement in motor gasoline quality.

Embodiments of the present disclosure further relate to any one or more of the following paragraphs:

1. A method for fluidized catalytic cracking, comprising: cracking one or more C2-C10 hydrocarbons in the presence of a catalyst under conditions sufficient to produce an effluent comprising ethylene, propylene, gasoline, and a coked-catalyst, wherein the catalyst comprises a first catalytic component having an average pore size of less than 6.4 Å and a second catalytic component having an average pore size of 6.4 Å or more; separating the effluent to provide a recovered coked-catalyst and a cracked product; and regenerating the recovered coked-catalyst to produce heat and the catalyst.

2. The method of paragraph 1, wherein the conditions comprise temperatures from about 590° C. to about 675° C. and pressures from about 68 kPa to about 690 kPa.

3. The method according to paragraph 1 or 2, wherein the first catalytic component has an average pore size from about 5 Å to about 6 Å.

4. The method according to any one of paragraphs 1 to 3, wherein the first catalytic component is ZSM-5.

5. The method according to any one of paragraphs 1 to 4, wherein the second catalytic component has an average pore size from about 6.4 Å to about 50 Å.

6. The method according to any one of paragraphs 1 to 5, wherein the second catalytic component is zeolite Y.

7. The method according to any one of paragraphs 1 to 6, wherein the second catalytic component is an active matrix component.

8. The method according to any one of paragraphs 1 to 7, wherein coke generated by the cracking is deposited on the catalyst to produce a coked-catalyst having from about 0.05 wt % to about 0.5 wt % coke on the catalyst.

9. The method according to any one of paragraphs 1 to 8, wherein the hydrocarbon has a sulfur concentration of less than 200 ppmw.

10. The method according to any one of paragraphs 1 to 9, wherein the hydrocarbon is substantially free of sulfur.

11. The method according to any one of paragraphs 1 to 10, wherein the gasoline has a diene concentration of less than about 0.5 wt %.

12. A method for fluidized catalytic cracking, comprising: cracking a hydrocarbon comprising C4-C8 hydrocarbons in the presence of a catalyst and a sulfur containing compound under conditions sufficient to produce an effluent comprising ethylene, propylene, gasoline, and a coked-catalyst, wherein the catalyst comprises a first catalytic component having an average pore size from about 5 Å to about 6 Å and a second catalytic component having an average pore size of 6.4 Å or more, and wherein the gasoline has a diene content of less than about 3 wt %; separating the effluent to provide a recovered coked-catalyst and a cracked product; and regenerating the recovered coked-catalyst to produce heat and the catalyst.

13. The method of paragraph 12, wherein the first and second conditions comprise a temperature from about 590° C. to about 675° C. and a pressure from about 68 kPa to about 690 kPa.

14. The method according to paragraph 12 or 13, wherein the first catalytic component is ZSM-5 and the second catalytic component is zeolite Y, USY, or an active matrix component.

15. The method according to any one of paragraphs 12 to 14, wherein the first catalytic component is ZSM-5 and the second catalytic component is peptized pseudoboehmite alumina.

16. The method according to any one of paragraphs 12 to 15, wherein the coked-catalyst comprises from about 0.05 wt % to about 0.5 wt % coke on the catalyst.

17. A method for fluidized catalytic cracking, comprising: cracking a hydrocarbon in the presence of a catalyst under conditions sufficient to produce an effluent comprising ethylene, propylene, gasoline, and a coked-catalyst, wherein the catalyst comprises a first catalytic component having an average pore size of about 5.2 Å to about 5.8 Å and a second catalytic component having an average pore size of 6.4 Å or more, and wherein the hydrocarbon comprises one or more C4-C8 hydrocarbons; separating the effluent to provide a recovered coked-catalyst comprising from about 0.05 wt % to about 0.5 wt % coke on the catalyst and a cracked product; and regenerating the recovered coked-catalyst to produce heat and the catalyst.

18. The method of paragraph 17, wherein the first catalytic component is ZSM-5 and the second catalytic component is zeolite Y.

19. The method according to paragraph 17 or 18, wherein the gasoline has a diene concentration of less than about 0.5 wt %.

20. The method according to any one of paragraphs 17 to 19, wherein the feed and the cracked product are substantially free of sulfur.

Certain embodiments and features have been described using a set of numerical upper limits and a set of numerical lower limits. It should be appreciated that ranges from any lower limit to any upper limit are contemplated unless otherwise indicated. Certain lower limits, upper limits, and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for fluidized catalytic cracking, comprising:
cracking a mixed C4 feed stream in the presence of a catalyst under conditions sufficient to produce an effluent comprising ethylene, propylene, gasoline, and a coked-catalyst, wherein the catalyst comprises a first catalytic component having an average pore size of less than 6.4 Å and a second catalytic component having an average pore size of 6.4 Å or more;
separating the effluent to provide a recovered coked-catalyst and a cracked product, wherein the coked-catalyst comprises between 1.5% and 5% coke by weight of the mixed C4 feed stream; and
regenerating the recovered coked-catalyst to produce heat and the catalyst.

2. The method of claim 1, wherein the conditions comprise temperatures from about 590° C. to about 675° C. and pressures from about 68 kPa to about 690 kPa.

3. The method of claim 1, wherein the first catalytic component has an average pore size from about 5 Å to about 6 Å.

4. The method of claim 1, wherein the first catalytic component is ZSM-5.

5. The method of claim 1, wherein the second catalytic component has an average pore size from about 6.4 Å to about 50 Å.

6. The method of claim 1, wherein the second catalytic component is zeolite Y.

7. The method of claim 1, wherein the second catalytic component is an active matrix component.

8. The method of claim 1, wherein the hydrocarbon has a sulfur concentration of less than 200 ppmw.

9. The method of claim 1, wherein the hydrocarbon is substantially free of sulfur.

10. The method of claim 1, wherein the gasoline has a diene concentration of less than about 0.5 wt %.

11. A method for fluidized catalytic cracking, comprising:
cracking a mixed C4 feed stream in the presence of a catalyst and a sulfur containing compound under conditions sufficient to produce an effluent comprising ethylene, propylene, gasoline, and a coked-catalyst, wherein the catalyst comprises a first catalytic component having an average pore size from about 5 Å to about 6 Å and a second catalytic component having an average pore size of 6.4 Å or more, and wherein the gasoline has a diene content of less than about 3 wt %;
separating the effluent to provide a recovered coked-catalyst and a cracked product, wherein the coked-catalyst comprises between 1.5% and 5% coke by weight of the mixed C4 feed stream; and
regenerating the recovered coked-catalyst to produce heat and the catalyst.

12. The method of claim 11, wherein the first and second conditions comprise a temperature from about 590° C. to about 675° C. and a pressure from about 68 kPa to about 690 kPa.

13. The method of claim 11, wherein the first catalytic component is ZSM-5 and the second catalytic component is zeolite Y, USY, or an active matrix component.

14. The method of claim 11, wherein the first catalytic component is ZSM-5 and the second catalytic component is peptized pseudoboehmite alumina.

15. A method for fluidized catalytic cracking, comprising:
cracking a mixed C4 feed stream in the presence of a catalyst under conditions sufficient to produce an effluent comprising ethylene, propylene, gasoline, and a coked-catalyst, wherein the catalyst comprises a first catalytic component having an average pore size of about 5.2 Å to about 5.8 Å and a second catalytic component having an average pore size of 6.4 Å or more, and wherein the hydrocarbon comprises one or more $C_4$-$C_8$ hydrocarbons;

separating the effluent to provide a recovered coked-catalyst and a cracked product, wherein the coked-catalyst comprises between 1.5% and 5% coke by weight of the mixed C4 feed stream; and regenerating the recovered coked-catalyst to produce heat and the catalyst.

16. The method of claim 15, wherein the first catalytic component is ZSM-5 and the second catalytic component is zeolite Y.

17. The method of claim 15, wherein the gasoline has a diene concentration of less than about 0.5 wt %.

18. The method of claim 15, wherein the feed and the cracked product are substantially free of sulfur.

\* \* \* \* \*